United States Patent [19]

Khan et al.

[11] Patent Number: 5,589,120
[45] Date of Patent: Dec. 31, 1996

[54] PROCESS OF MAKING A SHAPED TIP ON A CATHETER

[75] Inventors: Azhar J. Khan, West Valley City; David P. Hopkins, Salt Lake City; Mohammad A. Khan, Sandy, all of Utah

[73] Assignee: Becton Dickinson and Company, Franklin Lakes, N.J.

[21] Appl. No.: 443,649

[22] Filed: May 18, 1995

Related U.S. Application Data

[62] Division of Ser. No. 294,275, Aug. 22, 1994.

[51] Int. Cl.$^6$ .......................... B29C 43/02; B29C 43/52; B29C 57/00
[52] U.S. Cl. ............................................. 264/130; 264/322
[58] Field of Search ........................................ 264/130, 322

[56] References Cited

U.S. PATENT DOCUMENTS

| | | | |
|---|---|---|---|
| 3,574,673 | 4/1971 | Schweiger . | |
| 3,949,067 | 4/1976 | Gibbs | 424/73 |
| 4,588,398 | 5/1986 | Daugherty et al. | 604/265 |
| 4,661,300 | 4/1987 | Daugherty | 264/40.6 |
| 4,664,657 | 5/1987 | Williamitis et al. | 604/265 |
| 4,720,521 | 1/1988 | Spielvogel et al. | 524/862 |
| 4,758,595 | 7/1988 | Ogunbiyi et al. | 514/635 |
| 4,836,986 | 6/1989 | Ogunbiyi et al. | 422/28 |
| 4,838,876 | 6/1989 | Wong et al. | 604/265 |
| 4,842,889 | 6/1989 | Hu et al. | 427/38 |
| 4,844,986 | 7/1989 | Karakelle et al. | 428/447 |
| 4,904,433 | 2/1990 | Williamitis | 264/130 |
| 4,994,265 | 2/1991 | White | 424/73 |
| 5,013,717 | 5/1991 | Solomon et al. | 514/56 |
| 5,026,607 | 6/1991 | Kiezulas | 428/423 |
| 5,047,159 | 9/1991 | Zehler | 252/49.6 |
| 5,061,738 | 10/1991 | Solomon et al. | 523/100 |
| 5,185,006 | 2/1993 | Williamitis et al. | 604/265 |
| 5,266,359 | 11/1993 | Spielvogel | 427/388.4 |
| 5,272,012 | 12/1993 | Opolski | 428/423.1 |
| 5,338,312 | 8/1994 | Montgomery | 604/230 |
| 5,344,411 | 9/1994 | Domb et al. | 604/265 |
| 5,383,903 | 1/1995 | Totakura | 606/228 |
| 5,409,463 | 4/1995 | Thomas et al. | 604/167 |

OTHER PUBLICATIONS

Material Safety Data Sheet for: Y–12686 "Aminomodified Silicone–Polyether Copolymer", by Union Carbide Chemicals and Plastics Co., Inc., Danbury, CT, Effective Date Jun. 1, 1992.
Material Safety Data Sheet for: Y–12613 "Polyalkyleneoxidemethylsiloxane Copolymer", by Union Carbide Chemicals and Plastics Co., Inc., Danbury, CT, Effective Date: Sep. 17, 1992.
Material Safety Data Sheet for : "d,1–alpha–Tocopherol," by Hoffman–La Roche, Inc., Nutley, NJ, Effective Date: Jul. 20, 1992.
"Vitamin E in Dermatology", by W. Nikolowski, Vitamins, pp. 1–6, 1973.
Cosmocil® CQ brochure, by ICI Americas, Inc., 1986.
Baquacil brochure, by ICI Americas, Inc., 1986.
Silwet Surfactants brochure, by Union Carbide Chemicals and Plastics Company, Inc., 1988.
The United States Pharmacopeia, The National Formulary, Rockville, MD, pp. 1451–1453, 1990.

*Primary Examiner*—Leo B. Tentoni
*Attorney, Agent, or Firm*—Eric M. Lee, Esq.

[57] ABSTRACT

This invention relates to a process of making a shaped tip on a catheter. In this process, a lubricant solution is placed on a catheter, the catheter is placed on a mandrel, the catheter is heated, and the mandrel is engaged with a die to form a shaped tip on the catheter. The tipping lubricant of this invention comprises water as the solvent. The lubricant is a silicone surfactant, which is non-ionic and which is a good lubricating fluid. The lubricant solution into which the catheter is dipped includes low percentages of a solution stabilizer and an antimicrobial agent to clarify the solution and to inhibit microbial growth in the water solution. Vitamin E or its derivative may also be used in the lubrication solution.

16 Claims, No Drawings

PROCESS OF MAKING A SHAPED TIP ON A CATHETER

This is a division of application Ser. No. 08/294,275 filed Aug. 22, 1994.

BACKGROUND OF THE INVENTION

This invention relates in general to a tipping lubricant system used during the manufacture of intravenous (IV) catheters.

IV catheters are designed to infuse normal intravenous solutions, including antibiotics and other drugs, into a patient. These catheters are also used to withdraw blood from the patient for normal blood-gas analysis as well as other blood work. In order to insert an IV catheter into a patient, an introducer needle is used. The needle is typically stainless steel and is hollow. Its distal tip is ground to a sharp tip for easy insertion into the patient. The catheter is also hollow and is initially located coaxially around the introducer needle in an "over the needle" arrangement. The catheter is extruded out of suitable plastic material such as TEFLON material (polytetrafluoroethylene), polyvinyl chloride, polyethylene, polyurethane or polyether urethane. The internal diameter of the catheter tip is slightly less than the outer diameter of the tip of the needle so that the catheter tip has an interference fit on the needle tip. The interference fit is necessary so that when the catheter and introducer needle assembly is taken out of the package, the catheter remains snugly on the needle and does not easily slip off. This interference fit also facilitates insertion of the needle and catheter assembly into the patient's vein because it minimizes the chance that the catheter tip will fold over or peel back on the needle tip.

The shape of the catheter tip must produce minimal trauma to the patient during insertion of the catheter into the patient and while the catheter is in place in the patient. Such a preferred tip shape that provides these characteristics has a tapered outer wall and an angled tip and is disclosed in U.S. Pat. No. 4,588,398. A process for making that catheter tip is disclosed in U.S. Pat. No. 4,661,300. In this process, the catheter is placed on a mandrel. A die having an interior molding surface, which is tapered according to the tip desired on the catheter, is aligned axially with the mandrel. The catheter tip is heated, typically using RF energy, so that it is flowable. The mandrel and die are brought together so the distal edge of the mandrel engages the tapered portion of the die. This action cleanly forms a smooth and uniform tapered tip for the catheter.

After the catheter is tipped, it must be free of defects such as incomplete formation, substantial flash or jagged edges. The tip must also look smooth and be free of rollovers. In addition, the length of the catheter must remain within a desired specification after the tipping process. If, during the tipping process, the thermoplastic material sticks to the die or the mandrel, the length will vary greatly due to stretching and the tip will not be free of defects. Visual or microscopic examination may be used to determine if there are any tip defects and if the length of the catheter is within specifications.

Typically a lubricant is used to allow the tipped catheter to be easily removed from the mandrel and die. If a lubricant is not used, the tipped catheter could stick to the mandrel or die resulting in a deformed catheter when it is removed from the mandrel or die. Standard tipping lubricants include polydimethyl siloxanes such as Dow Corning DC 360 or curable silicones such as Dow Corning 44159 MDX which are amine terminated and moisture curable. Non-curable amine terminated polydimethyl siloxanes have also been used for this purpose. Such lubricants are described in, for example, U.S. Pat. Nos. 3,574,673; 4,904,433; and 5,185,006.

The amount of lubricant needed to provide lubricity between the catheter and the mandrel and die is very small. Thus in order to control the application of the lubricant, the catheter is dipped into a solution including the lubricant. Use of a solution also facilitates application of the lubricant to the inside surface as well as outside surface of the catheter. The silicone oils used as typical lubricants are hydrophobic. Therefore, these compounds must be dissolved in organic solvents in order to prepare a solution in which the catheter tip can be dipped for lubrication before tipping can begin. The primary solvent that has been used is freon because it is nonflammable and evaporates quickly. Unfortunately, because of recent concerns that chlorofluorocarbons (CFC) react with and destroy the earth's protective ozone layer, the production and use of CFC will cease in the near future. Thus other solvents must be used. Other organic solvents, such as alcohols and hydrocarbons, are highly flammable and are not desirable.

SUMMARY OF THE INVENTION

It is therefore an object of this invention to provide a tipping lubricant that does not require the use of a CFC as a solvent.

It is another object of this invention to provide a tipping lubricant solution that is "environmentally friendly".

It is still another object of this invention to provide a tipping lubricant solution that is not flammable.

The tipping lubricant solution of this invention comprises water as the solvent. The lubricant is a silicone surfactant, which is a good lubricating fluid. In addition, it is preferable that non-ionic silicone surfactants be used because they may have lower toxicity. The lubricant solution into which the catheter is dipped includes low percentages of a solution stabilizer and an antimicrobial agent to clarify the solution and to inhibit microbial growth in the water solution. In addition, the lubricant solution may also include vitamin E or its derivative.

The above and other objects and advantages of the invention will be apparent upon consideration of the following detailed description.

DETAILED DESCRIPTION OF THE INVENTION

Although this invention is described in terms of its application to IV catheters and introducer needles, it is to be understood that this invention could be used on other medical devices where a lubricious surface on the device is desirable.

The tipping lubricant solution of this invention is a solution of a silicone surfactant, vitamin E or its derivative, cosmocil and water. Preferably the silicone surfactant is a polyalkyleneoxide dimethylsiloxane copolymer such as the Silwet silicone surfactant sold by OSI Specialties, Inc. These surfactants are block copolymer polyalkylene oxide-modified polydimethylsiloxanes. They are similar to standard silicone fluids except the polydimethylsiloxane backbone has polyalkylene oxide side chains similar to non-ionic surfactants such as poly (oxyethylene) poly (oxypropylene)

block copolymers known as pluronic polyols. The side chains are terminated with hydroxy or low alkoxy end groups. The molecular structure of the Silwet L7001 silicone surfactant is shown below.

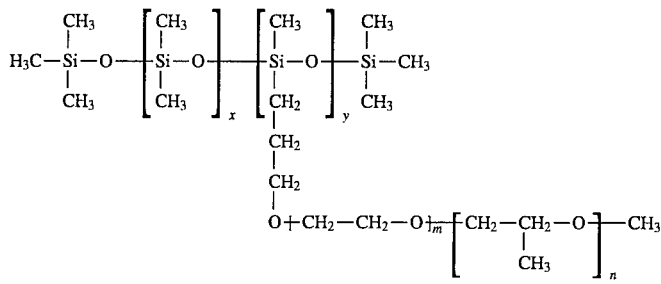

This silicone surfactant has a molecular weight of 20,000 and a viscosity of 1700 centistokes and it is soluble in water. Preferably between about 2% and about 6% of the silicone surfactant is used in the lubricant solution. A combination of the undiluted base silicone surfactant and the undiluted amino-modified base silicone surfactant may be used as the lubricant. When a combination of the amino-modified base silicone surfactant and the undiluted base silicone surfactant are used as the lubricant, preferably between about 2% and about 6% of the combination is used in the solution. Alternatively, the amino-modified base silicone surfactant can be used alone as the lubricant. In this case, between about 2% and about 6% of the amino-modified base silicone surfactant is used in the solution.

Vitamin E is chemically known as alpha-tocopherol and is an antioxidant. Since vitamin E is an antioxidant it prevents degradation of the lubricated solutions through oxidation and thus minimizes the effects of aging. In addition, vitamin E and its derivative, vitamin E acetate, enhance the lubricity of the lubricant of this invention. Preferably between 0.1% and 1% of vitamin E or its derivative, vitamin E acetate, is used. The molecular structure of vitamin E is shown below:

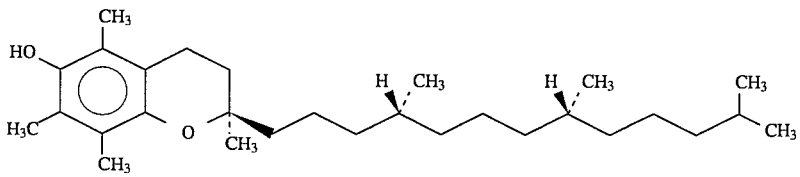

Cosmocil, polyhexamethylene biguanide hydrochloride, is an excellent solution stabilizer and antimicrobial agent which inhibits microbial growth in the water solution or on the coated product. Preferably about 1% to about 5% of cosmocil is used. Other antimicrobial agents that can be used include: iodophors; phenols; phenolic compounds such as para-chloro-meta-xylenol; and other biguanides such as chlorhexidine gluconate. Cosmocil is preferably used because it is less toxic than the other anti-microbial agents. Its molecular structure is shown below:

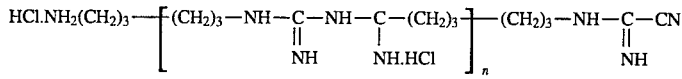

Catheter blanks to be tipped can be dipped into the neat, i.e. 100%, lubricant. Preferably the catheter blanks may be dipped into the lubrication solution of this invention. Only the tip portion of the catheter need be dipped into the solution. The duration of the dipping step is not critical. The lubrication solution may also be applied by brushing or spraying. The solvent may be removed by ambient evaporation or warming.

After the lubrication solution is applied, the catheter is mounted on a mandrel and heated. A die and the mandrel are brought into engagement to form the catheter tip. The tipped catheter is then easily and quickly removed from the die and mandrel.

EXAMPLE NO. 1

The following table identifies the effects of using different amounts of a silicone surfactant and an amino-modified silicone surfactant as the lubricant.

|  | 1 | 2 | 3 | 4 |
|---|---|---|---|---|
| Silicone surfactant (%) | 3.00 | 3.00 | 4.50 | 3.00 |
| Amino-modified silicone surfactant (%) | 0.00 | 0.25 | 0.00 | 0.50 |
| Vitamin E (%) | 0.125 | 0.00 | 0.25 | 0.125 |
| Cosmocil (PPM) | 50 | 50 | 50 | 50 |
| Water (%) | 96.88 | 96.75 | 95.25 | 96.38 |
| No. of Tips Sticking (out of 60) | 8 | 0 | 1 | 0 |
| Catheter Length | 1.99866 | 2.00030 | 1.99953 | 1.99993 |

-continued

|  | 1 | 2 | 3 | 4 |
|---|---|---|---|---|
| (inches) (Target length is 2.0 inches) | | | | |

If the catheter tip sticks, the catheter length will not be 2.0 inches due to stretching of the catheter tip as it is removed from the mandrel. As can be seen, when the lubricant provided adequate lubricity, no tips stuck to the mandrel and the catheter length was very close to the target length of 2 inches.

If the adhesion between the catheter tip and the introducer needle is too high, the needle cannot be easily withdrawn from the catheter after the assembly is placed into the patient's vein. Many thermoplastic materials such as polyurethanes are very sticky in nature and will bond to the surface of a metal under compression. Since the catheter tip sits over the stainless steel needle with an interference fit, it will stick to the needle unless the needle is lubricated.

EXAMPLE NO. 2

The following lubricants were used during the tipping process as a tipping lubricant and to lubricate the needle and the catheter. The control group is included for comparison.

|  | Tipping Lube | Needle Lube | Catheter Lube |
|---|---|---|---|
| Silicone surfactant (%) | 2.375 ± 0.25 | 2.375 ± 0.25 | 4.75 ± 0.25 |
| Amino-modified silicone surfactant (%) | 0.525 ± 0.025 | 0.525 ± 0.025 | 0.525 ± 0.025 |
| Vitamin E (%) | 0.2625 ± 0.0125 | 0.2625 ± 0.0125 | 0.2625 ± 0.0125 |
| Cosmocil (PPM) | 50 | 50 | 50 |
| Water (%) | 96.8375 ± 0.2875 Control | 98.8375 ± 0.2875 | 94.4625 ± 0.2875 |
| DC 12600 cstk Silicone (%) | — | — | 2.0 |
| Masil 1 MM cstk Silicone (%) | — | 2.4 | — |
| PS-5I 3 Amino-modified Silicone (%) | 0.5 | — | — |
| HCPC-14lb, Genesolve 2000 (%) | 99.5 | 97.6 | 98.0 |

20 gauge (ga) catheter products were assembled by using the catheter tipping lubricant for tipping the catheter first, lubricating the needle and catheter separately using the respective lubricants and finally assembling the catheter assembly. The products were aged at 90° C. for two weeks and tested for tip adhesion. The products were also penetration tested through latex membrane 13.5 mils thick. The results are described below:

|  | Control | | Test | |
|---|---|---|---|---|
| Aging | Tip Adhesion (lbs) | Catheter Drag (g) | Tip Adhesion (lbs) | Catheter Drag (g) |
| 0 Week | 0.19 | 3.0 | 0.12 | 4.8 |
| 1 week, 90° C. | 0.10 | 4.0 | 0.11 | 3.6 |
| 2 week, 90° C. | 0.16 | 3.9 | 0.12 | 4.7 |

From the above data, it is clear that the lubricant of this invention stabilizes tip adhesion and the catheter lubricant lubricates the catheter adequately. Furthermore, the properties of the lubricant of this invention are comparable to the control products.

EXAMPLE NO. 3

Other silicone surfactant combinations have been tried. For example, a polyalkylene oxide-modified polydimethylsiloxane block copolymer known as Silwet L7230 which is similar to Silwet L7001 was used in combination with an amino-modified silicone-polyether copolymer known as Silwet Y12593.

| Ingredients | Waterborne Lubricant | Silicone 1 MM cstk |
|---|---|---|
| Silwet L7230 (%) | 4.50 | — |
| Silwet Y12593 (%) | 0.50 | — |
| Vitamin E (%) | 0.25 | — |
| Water (%) | 94.75 | — |
| Silicone 1 MM cstk (%) | — | 2.4 |
| Freon TF (%) | — | 97.6 |

The catheter tubing is wedged into the catheter adapter by using stainless steel wedges. When the catheter assembly is put over the needle assembly it is possible that the stainless steel wedge and the stainless steel needle may rub. Thus there could exist a high resistive force between the two metal surfaces. This becomes even more prominent when the catheter is pushed off of the needle depending upon the angle between the catheter tubing and the needle. A test was devised in which the catheter was held stationary at certain angle rotations to make sure that the needle is rubbing the wedge. The needle was pulled out and the resistive force was measured. The results are given below:

| Product Tested | Resistive Force (lbs) |
|---|---|
| Unlubricated 20(ga) catheter | 0.400 |
| 20(ga) Catheter Lubricated with Silicone | 0.160 |
| 20(ga) Catheter Lubricated with Lubricant of this invention | 0.078 |

The data clearly shows the lubricant effectiveness of the water soluble lubrication system of this invention.

EXAMPLE NO. 4

A quaternary ammonium salt was used as a solution stabilizer for the tipping lubricant solution to ensure that the solution is homogenous. A lubricant containing 3% Silwet L7001, 0.5% Sylguard, which is a reactive quat, 0.25% Urea, and 96.25% water was used for tipping catheters. In all products tested, the tip quality was acceptable. Other quaternary ammonium salts such as benzethonium chloride could also be used.

EXAMPLE NO. 5

Different amounts of an amino-modified silicone-polyether were used to establish an acceptable range for use as a tipping lubricant.

|  | 1 | 2 |
|---|---|---|
| Amino-modified silicone surfactant (g) | 1.0 | 10.0 |
| Water (g) | 99.0 | 90.0 |

| | 1 | 2 |
|---|---|---|
| Tip Quality | Good | Good |

Thus, it is seen that a new tipping lubricant is provided that does not require the use of CFC as a solvent and is thus "environmentally friendly." The lubricant solution is also non-flammable.

We claim:

1. A method for forming a shaped tip on a catheter comprising:

applying a tipping lubricant solution containing a silicone surfactant and water to a tip of an untipped catheter tubing:

placing the untipped catheter tubing on a mandrel;

heating the untipped catheter tubing;

engaging the mandrel with a die to form the catheter tip; and removing the shaped catheter tubing from the die and mandrel.

2. The method of claim 1 wherein the silicone surfactant is a block copolymer polyalkylene oxide-modified polydimethylsiloxane.

3. The method of claim 2 wherein the block copolymer polyalkylene oxide-modified polydimethylsiloxane comprises between about 2% and about 6% of the solution.

4. The method of claim 2 wherein the silicone surfactant also includes an amino-modified silicone polyether copolymer.

5. The method of claim 4 wherein the amino-modified silicone polyether copolymer comprises between about 2% and about 6% of the solution.

6. The method of claim 1 wherein the silicone surfactant is an amino-modified silicone polyether copolymer.

7. The method of claim 6 wherein the amino-modified silicone polyether copolymer comprises between about 2% and about 6% of the solution.

8. The method of any of claims 1–7 wherein the solution also includes vitamin E or its derivative.

9. The method of claim 8 wherein the vitamin E or its derivative comprises between about 0.1% and about 1% of the solution.

10. The method of claim 8 wherein the solution includes a solution stabilizer.

11. The method of claim 10 wherein the solution stabilizer is selected from the group consisting of a quaternary ammonium salt and polyhexamethylene biguanide hydrochloride.

12. The method of claim 11 wherein the solution stabilizer comprises between about 1% and about 5% of the solution.

13. The method of any of claims 1–7 or 9–12 wherein the solution also includes an anti-microbial agent.

14. The method of claim 13 wherein the anti-microbial agent is selected from the group consisting of iodophors, phenols, phenolic compounds, and biguanides.

15. The method of claim 8 wherein the solution also includes an anti-microbial agent.

16. The method of claim 15 wherein the anti-microbial agent is selected from the group consisting of iodophors, phenols, phenolic compounds and biguanides.

* * * * *